US009933409B2

(12) United States Patent
Wittekind, III (10) Patent No.: US 9,933,409 B2
(45) Date of Patent: Apr. 3, 2018

(54) STRIP CONNECTOR WITH RELIABLE INSERTION AND EJECTION

(75) Inventor: Frederick Leland Wittekind, III, Anderson, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 1905 days.

(21) Appl. No.: 13/296,659

(22) Filed: Nov. 15, 2011

(65) Prior Publication Data
US 2013/0122736 A1 May 16, 2013

(51) Int. Cl.
*H01R 13/64* (2006.01)
*H01R 24/60* (2011.01)
*G01N 33/487* (2006.01)

(52) U.S. Cl.
CPC ... *G01N 33/4875* (2013.01); *G01N 33/48785* (2013.01)

(58) Field of Classification Search
CPC .............. G01N 33/4875; G01N 33/48785
See application file for complete search history.

(56) References Cited

U.S. PATENT DOCUMENTS

| 4,934,817 | A  | * | 6/1990  | Gassenhuber | ......... | G01N 33/92 |
|-----------|----|---|---------|-------------|-----------|------------|
|           |    |   |         |             |           | 356/244    |
| 6,200,442 | B1 | * | 3/2001  | Markart     | ............. | G01N 33/4875 |
|           |    |   |         |             |           | 204/400    |
| 7,351,212 | B2 |   | 4/2008  | Roe         |           |            |
| 7,585,464 | B2 |   | 9/2009  | Amano et al.|           |            |
| 7,641,777 | B2 |   | 1/2010  | Joseph et al.|          |            |
| 7,731,900 | B2 |   | 6/2010  | Haar et al. |           |            |
| 7,754,152 | B2 |   | 7/2010  | Riebel et al.|          |            |
| 7,758,518 | B2 |   | 7/2010  | Perez et al.|           |            |
| 7,819,283 | B2 |   | 10/2010 | Chambers et al.|        |            |
| 7,909,776 | B2 |   | 3/2011  | Roe et al.  |           |            |
| 7,927,291 | B2 |   | 4/2011  | Roe         |           |            |
| 7,955,271 | B2 |   | 6/2011  | Roe et al.  |           |            |
| 8,002,785 | B2 |   | 8/2011  | Weiss et al.|           |            |

(Continued)

FOREIGN PATENT DOCUMENTS

| EP | 1 321 769 A1 | 6/2003 |
|----|--------------|--------|
| EP | 1 382 968 A1 | 1/2004 |

(Continued)

*Primary Examiner* — Rene Towa
(74) *Attorney, Agent, or Firm* — Woodard, Emhardt, Moriarty, McNett & Henry LLP (57) ABSTRACT

A strip connector includes a connector housing having a housing cavity and guide feature. A strip carrier slidable in the housing cavity includes a carrier body having a strip channel slidably receiving a test strip in an insertion direction. A first biasing member biases the strip carrier in an ejection direction opposite the insertion direction. A second biasing member acting orthogonal to the first biasing member biases the carrier body in a contact direction orthogonal to the ejection direction. First and second male members of the carrier body slide with respect to the guide feature and prevent strip contact direction carrier displacement until the male members are axially aligned with guide feature branches extending orthogonally to the guide feature. A test strip conductor contacts connector housing electrical contacts when the male members axially align with the branches and the second biasing member displaces the strip carrier in the contact direction.

26 Claims, 9 Drawing Sheets

(56) References Cited

U.S. PATENT DOCUMENTS

| | | | |
|---|---|---|---|
| 2005/0101981 A1* | 5/2005 | Alden | A61B 5/150748 606/181 |
| 2005/0224345 A1 | 10/2005 | Taniike et al. | |
| 2005/0277850 A1* | 12/2005 | Mace | A61B 5/1411 600/584 |
| 2007/0170200 A1 | 7/2007 | Chambers et al. | |
| 2007/0249921 A1 | 10/2007 | Groll et al. | |
| 2008/0229808 A1 | 9/2008 | Lee | |
| 2009/0209040 A1 | 8/2009 | Flora et al. | |
| 2010/0012530 A1 | 1/2010 | Watanabe et al. | |
| 2011/0040160 A1 | 2/2011 | Sakata et al. | |
| 2011/0143562 A1 | 6/2011 | Wu et al. | |
| 2011/0186588 A1 | 8/2011 | DeAngeli et al. | |
| 2011/0189062 A1 | 8/2011 | DeAngeli et al. | |
| 2011/0278321 A1* | 11/2011 | Chan | A61B 5/14532 221/198 |
| 2012/0109176 A1* | 5/2012 | Roe | A61B 5/1411 606/182 |

FOREIGN PATENT DOCUMENTS

| | | |
|---|---|---|
| EP | 1 480 037 A1 | 11/2004 |
| EP | 1 321 769 B1 | 7/2006 |
| EP | 1 762 848 A1 | 3/2007 |
| EP | 1 983 339 A1 | 10/2008 |
| EP | 1 382 968 B1 | 11/2008 |
| EP | 1 762 848 B1 | 11/2008 |
| EP | 2 071 326 A1 | 6/2009 |
| JP | 2003-114213 | 4/2003 |
| JP | 2004-101514 | 4/2004 |
| WO | WO 02/08753 A2 | 1/2002 |
| WO | WO 02/08753 A3 | 1/2002 |
| WO | WO 2004/063747 A1 | 7/2004 |
| WO | WO 2005/080966 A1 | 9/2005 |
| WO | WO 2007/083773 A1 | 7/2007 |
| WO | WO 2008/016137 A1 | 2/2008 |
| WO | WO 2009/055643 A2 | 4/2009 |
| WO | WO 2009/055643 A3 | 4/2009 |

* cited by examiner

STRIP CONNECTOR WITH RELIABLE INSERTION AND EJECTION

FIELD

The present disclosure relates generally to bodily fluid sampling devices and more specifically, but not exclusively, to a strip connector that provides an orthogonal displacement of the test strip during insertion to directly connect with the electrical contacts.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Medical devices are often used as diagnostic devices and/or therapeutic devices in diagnosing and/or treating medical conditions of patients. For example, a blood glucose meter is used as a diagnostic device to measure blood glucose levels of patients suffering from diabetes. Blood glucose meters use a test strip that receives a blood sample of the patient. The test strip has electrical contacts on the strip that are electrically contacted when the test strip is inserted into the meter. The meter determines a blood glucose level by measuring currents passed through the electrical contacts of the strip, and provides a readout of the glucose level.

Known meters receive the test strip in an insertion direction that also engages the electrical strip conductors of the test strip with the electrical contacts of the meter. Once initial contact is made by the electrical contacts, the thin gold or conductive metal layer applied to the strip conductors may be displaced as the strip continues in the insertion direction until reaching a stop location. Poor electrical contact can result if the conductive metal layer is displaced with respect to the electrical contacts. This can result in error messages being received by the patient, and the need to repeat the sampling/test procedure.

SUMMARY

According to the present disclosure, a strip connector receiving a body fluid test strip to measure a biologic fluid applied to the test strip includes a connector housing having a housing cavity. A strip carrier is movably disposed in the housing cavity of the connector housing. The strip carrier includes a carrier body having a longitudinal strip channel configured to slidably receive a body fluid test strip in an insertion direction. A first biasing member positioned between the strip carrier and the connector housing acts to bias the strip carrier in an ejection direction oppositely directed with respect to the insertion direction. A second biasing member is positioned between the strip carrier and the connector housing and acts orthogonally with respect to the first biasing member. The second biasing member acts to bias the carrier body in a contact direction orthogonally oriented with respect to the ejection direction.

Also according to the present disclosure, a strip connector receiving a body fluid test strip to measure a biologic fluid applied to the test strip includes a connector housing having a housing cavity and a guide feature. A strip carrier slidably disposed in the housing cavity of the connector housing includes a carrier body having a longitudinal strip channel configured to slidably receive a test strip in an insertion direction. A first biasing member is positioned between the strip carrier and the connector housing acting to bias the strip carrier in an ejection direction oppositely directed with respect to the insertion direction. At least one second biasing member contacting the carrier body and in sliding contact with the connector housing acts orthogonally with respect to the first biasing member and acts to bias the carrier body in a contact direction orthogonally oriented with respect to the ejection direction. A male member outwardly extending from the carrier body is slidably received in the guide channel created in the connector housing. The male member contacts a wall of the guide channel preventing displacement of the strip carrier in the contact direction until the male member is axially aligned with and received in a guide channel branch extending orthogonally with respect to the guide channel, that alignment corresponding to alignment of the strip conductors with their respective target electrical contacts.

Further according to the present disclosure, a strip connector receiving a body fluid test strip to measure a biologic fluid applied to the test strip includes a connector housing having a housing cavity. A strip carrier is slidably disposed in the housing cavity of the connector housing. The strip carrier includes a carrier body having: a longitudinal strip channel configured to slidably receive a test strip in an insertion direction; a first biasing member acting to bias the strip carrier in an ejection direction oppositely directed with respect to the insertion direction; and a second biasing member in a first mode orthogonally acting with respect to the first biasing member. The second biasing member acts to bias the carrier body in a contact direction orthogonally oriented with respect to the ejection direction. The second biasing member in a second mode is further partially deflected by motion of the strip carrier in the insertion direction to bias the carrier body in the ejection direction together with the first biasing member. The biasing members are normally unstressed in a "home" position (strip carrier ready to receive a strip) to prevent premature spring force reduction due to relaxation that could occur if the biasing members were in a state of continuous deflection.

Additionally, according to the present disclosure a strip connector receiving a body fluid test strip to measure a biologic fluid applied to the test strip includes a connector housing having a housing cavity. A strip carrier movably disposed in the housing cavity includes a carrier body having a longitudinal strip channel configured to slidably receive a test strip in an insertion direction. A first biasing member acts to bias the strip carrier in an ejection direction oppositely directed with respect to the insertion direction. A second biasing member contacting the carrier body acts orthogonally with respect to the first biasing member to bias the carrier body in a contact direction orthogonally oriented with respect to the ejection direction. At least first and second electrical contacts connected to the connector housing are each individually contacted by a strip conductor of the test strip when the strip carrier is displaced in the contact direction by the second biasing member.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

Figure 1:
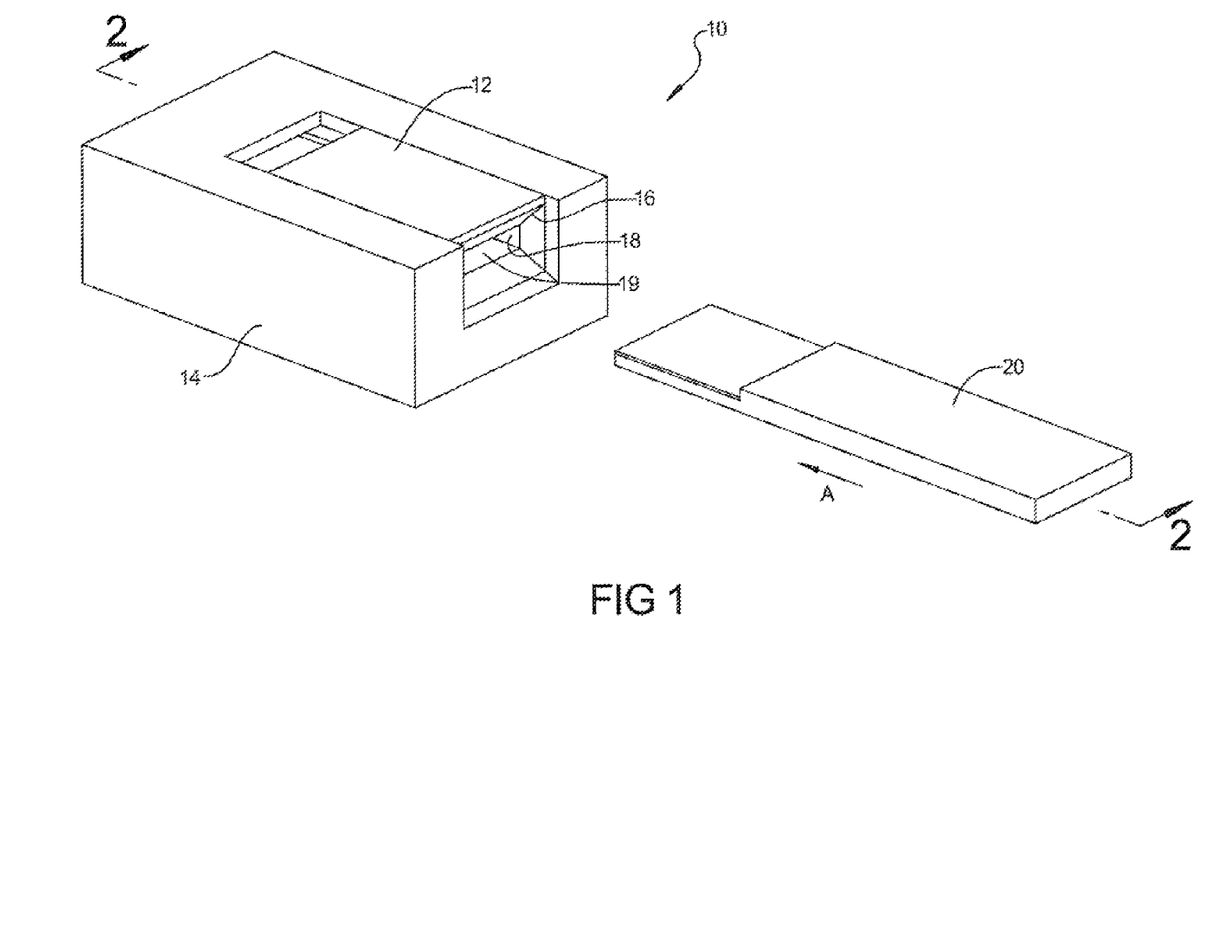
FIG. 1 shows a perspective view of an exemplary strip connector device of the present disclosure adapted to receive and eject test strips.

Referring to FIG. 1, a strip connector device 10 includes a strip carrier 12 which is received in and is slidably displaced with respect to a connector housing 14. Strip carrier 12 includes a carrier body 16 having a channel opening 18 defining a longitudinal strip channel 19. A test strip 20 is shown prior to being slidably received in an insertion direction "A" into channel opening 18 by the user of the strip connector device 10. Strip 20 is manually inserted into channel opening 18 and substantially through longitudinal strip channel 19.

Figure 2:
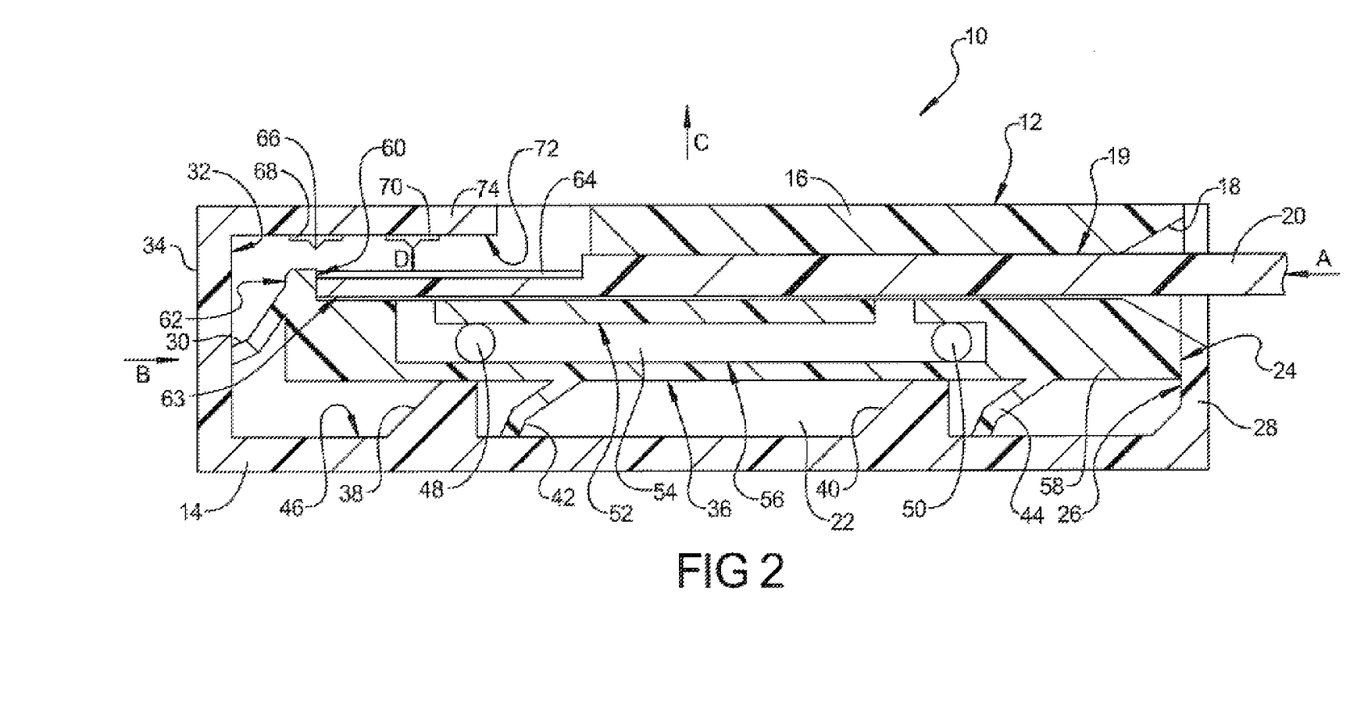
FIG. 2 shows a cross sectional side elevational view taken at section 2 of FIG. 1 showing a carrier body stop position.

Referring to FIG. 2, strip connector device 10 further includes a housing cavity 22 of connector housing 14 within which carrier body 16 is slidably disposed. In a strip loaded condition shown, strip 20 is manually inserted in the insertion direction "A" until strip 20 completely fills the longitudinal strip channel 19. Prior to and during insertion of strip 20, a carrier body first end face 24 of carrier body 16 is biased into contact with a housing first end face 26 of a housing first end wall 28 of connector housing 14. Contact between carrier body first end face 24 and housing first end face 26 is normally maintained by a biasing force created by a first biasing member 30 positioned between and contacting both carrier body 16 and a housing second end face 32 of a housing second end wall 34 of connector housing 14.

Carrier body 16 further includes a carrier body support wall 36 defining a planar surface of carrier body 16. During sliding receipt of strip 20, carrier body support wall 36 is freely spaced with respect to planar faces of each of a first raised stop 38 and a second raised stop 40, both upwardly extending into body cavity 22 from connector housing 14 and integrally connected to connector housing 14. This spacing ensures less frictional resistance for sliding motion of the carrier body 16. At least a second biasing member 42 and according to several aspects a third biasing member 44 are each positioned between and contact both carrier body 16 and a housing lower wall face 46 of connector housing 14. According to several embodiments, second and third biasing members 42, 44 are integrally connected to carrier body 16 and can be co-molded with carrier body 16 when carrier body 16 is created of a polymeric material. According to additional embodiments (not shown), second and third biasing members 42, 44 can be connected to, but not integrally provided with, carrier body 16, or connected to housing lower wall face 46 of connector housing 14. First, second and third biasing members 30, 42 and 44 can also take the form of coiled compression springs or leaf springs. In the strip receiving condition shown, the biasing force created by first biasing member 30 acts to bias carrier body 16 in an ejection direction "B" such that contact between carrier body first end face 24 and housing first end face 26 is maintained in this condition. Conversely and acting orthogonally with respect to first biasing member 30, in a first mode the second and third biasing members 42, 44 are spaced from or can slidingly contact housing lower wall face 46 of connector housing 14 and are maintained in a non-deflected or substantially non-deflected condition as carrier body 16 slides in either the insertion direction "A" or ejection direction "B". The second and third biasing members 42, 44 are subsequently deflected, thereby creating a biasing force acting to displace carrier body 16 in a contact direction "C" orthogonally oriented with respect to ejection direction "B", by contact with first and second raised stops 38, 40. First, second and third biasing members 30, 42 and 44 are normally unstressed in a "home" position (defined when the strip carrier 12 is ready to receive a strip 20) to prevent premature spring force reduction due to relaxation that could occur if the biasing members were in a state of continuous deflection.

In the carrier body stop position, the biasing force created by each of the second and third biasing members 42, 44 acting in the contact direction "C" is prevented from displacing carrier body 16 in the contact direction "C" by direct contact between each of a first and a second male members or guide rod 48, 50 with a guide feature upper face 52 of a longitudinal guide feature 54 which can by non-limiting example take the form of a recessed slot, an elongated travel path having external raised or recessed walls, or a U-shaped guide channel. Longitudinal guide feature 54 is created in a sidewall (not visible in this view) of connector housing 14. Each of the first and second guide rods 48, 50 are slidably received in longitudinal guide feature 54 and are in sliding contact with each of guide feature upper face 52 and a guide feature lower face 56. Each of the first and second guide rods 48, 50 are integrally connected to and extend horizontally outward (toward the viewer as shown in FIG. 2) from a body lower portion 58 of carrier body 16.

In the carrier body stop position, strip 20 which was inserted in the insertion direction "A" is brought into direct contact with a strip contact wall 60 positioned opposite with respect to a carrier body second end face 62 from which first biasing member 30 extends. When strip 20 is in direct contact with strip contact wall 60, strip 20 is also supported by a channel lower surface 63 of longitudinal strip channel 19. In the carrier body stop position, at least one and according to several embodiments a plurality of strip conductors 64 of strip 20 are oriented facing, but having a clearance space with respect to a barb end 66 of each of a first and second set of electrical contacts 68, 70. The electrical contacts 68, 70 can be individual contacts, positioned in rows each having single or multiple contacts each, or similar configurations. According to several embodiments, first and second contacts 68, 70 are fixedly connected to a housing upper wall face 72 of a housing upper wall 74 of connector housing 14. Also in the carrier body stop position, a contact clearance "D" is maintained between strip conductors 64 and the barb end 66 of each of first and second contacts 68, 70 to prevent electrical or mechanical contact between any of the first or second contacts 68, 70 and the strip conductors 64. As previously noted, the first and second guide rods 48, 50 which contact the guide feature upper face 52 of guide feature 54 prevent the biasing force created by second and third biasing members 42, 44 from displacing carrier body 16 in the contact direction "C" at this time. According to further aspects, in lieu of barb end 66 used for each of the first and second electrical contacts 68, 70, first and second contacts 68, 70 can be looped or deflectable members which are elastically deflected when strip conductors 64 are brought into contact with the first and second electrical contacts 68, 70.

Referring to FIG. 3 and again to FIG. 2, after the strip 20 contacts strip contact wall 60 at a strip contact end 76, the user continues to manually push strip 20 in the insertion direction "A", thereby further deflecting the first, second, and third biasing members 30, 42, 44 until a carrier body stop position shown is reached. The carrier body stop position is defined when first guide rod 48 contacts a guide feature end wall 78 of guide feature 54. At this time and in a second mode, each of the second and third biasing members 42, 44 are additionally deflected and therefore further biased by contact with each of the first and second raised stop end faces 88, 90 creating an additional biasing force acting in ejection direction "B". The additional biasing force of second and third biasing members 42, 44 acting in ejection direction "B" therefore adds to the biasing force of first biasing member 30 in the ejection direction "B". The second and third biasing members 42, 44 also continue to bias carrier body 16 in the contact direction "C". Therefore, according to several aspects, second and third biasing members 42, 44 can create biasing forces acting in each of the ejection direction "B" and the contact direction "C". When first guide rod 48 directly contacts guide feature end wall 78, first guide rod 48 is in axial alignment with a guide feature first branch 80. At the same time, the second guide rod 50 is in axial alignment with a guide feature second branch 82. First guide rod 48 is therefore coaxially aligned with a first branch axial centerline 84, and second guide rod 50 is coaxially aligned with a second branch axial centerline 86 in the carrier body stop position.

Figure 3:
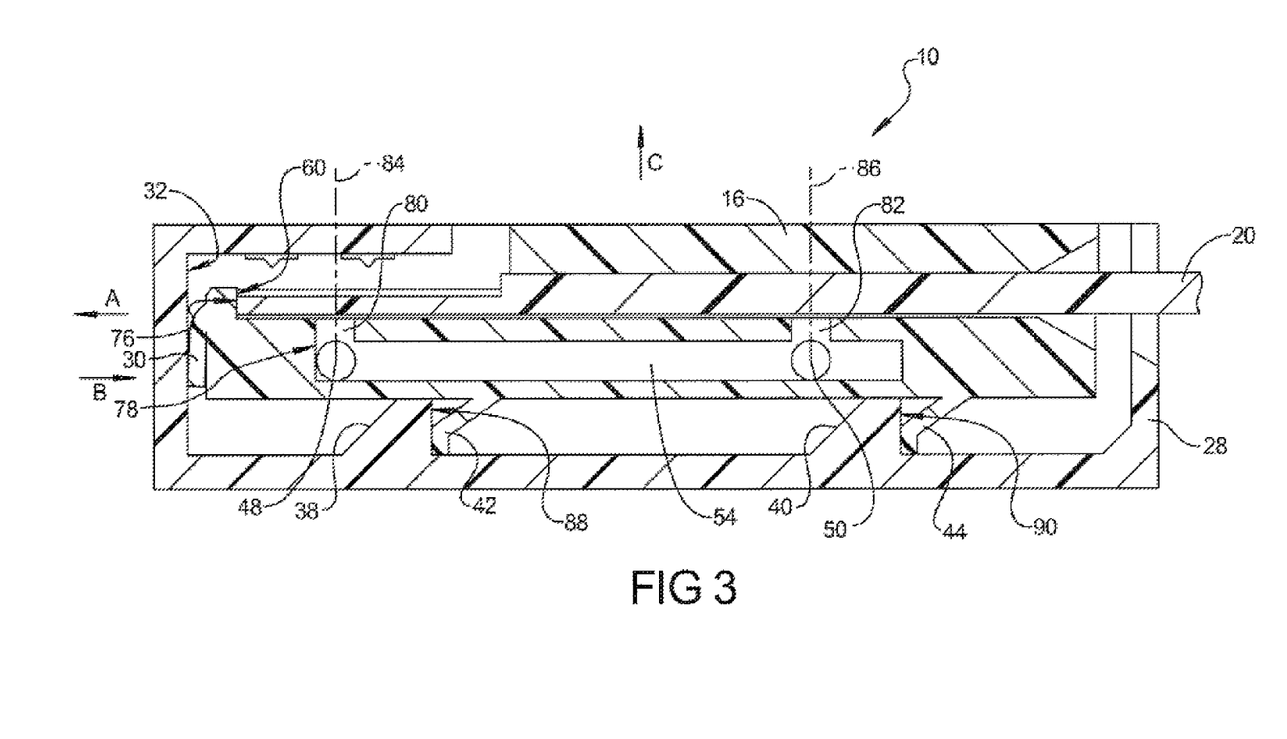
FIG. 3 shows a cross sectional side elevational view modified from FIG. 2 to show a test strip/carrier body displaced condition.

Referring to FIG. 4 and again to FIG. 3, as soon as the first and second guide rods 48, 50 are aligned with the individual guide feature first and second branches 80, 82 defining the strip conductor alignment position, a portion of the biasing force of second and third biasing members 42, 44 acts to displace carrier body 16 in the contact direction "C". This displacement of carrier body 16 forces the strip conductors 64 of strip 20 into direct contact with the barb end of each of first and second contacts 68, 70, thereby defining a strip conductor contact position. The barb end of the first and second contacts 68, 70 is forced into a gold coating layer of the strip conductors 64 only in the contact direction "C", which minimizes horizontal displacement of the gold material layer of strip conductors 64. The geometry of each of the guide feature first and second branches 80, 82 is selected to slidably receive the first and second guide rods 48, 50, but not allow horizontal displacement of the carrier body 16 in either of the insertion direction "A" or ejection direction "B" while the first and second guide rods 48, 50 are received in individual ones of the guide feature first and second branches 80, 82. This ensures that the carrier body 16 only moves in the contact direction "C" to make electrical contact with the first and second contacts 68, 70. During the time period when carrier body 16 is displaced in the contact direction "C", the second and third biasing members 42, 44 can either remain in direct contact with the first and second raised stop end faces 88, 90 or be displaced therefrom.

Figure 4:
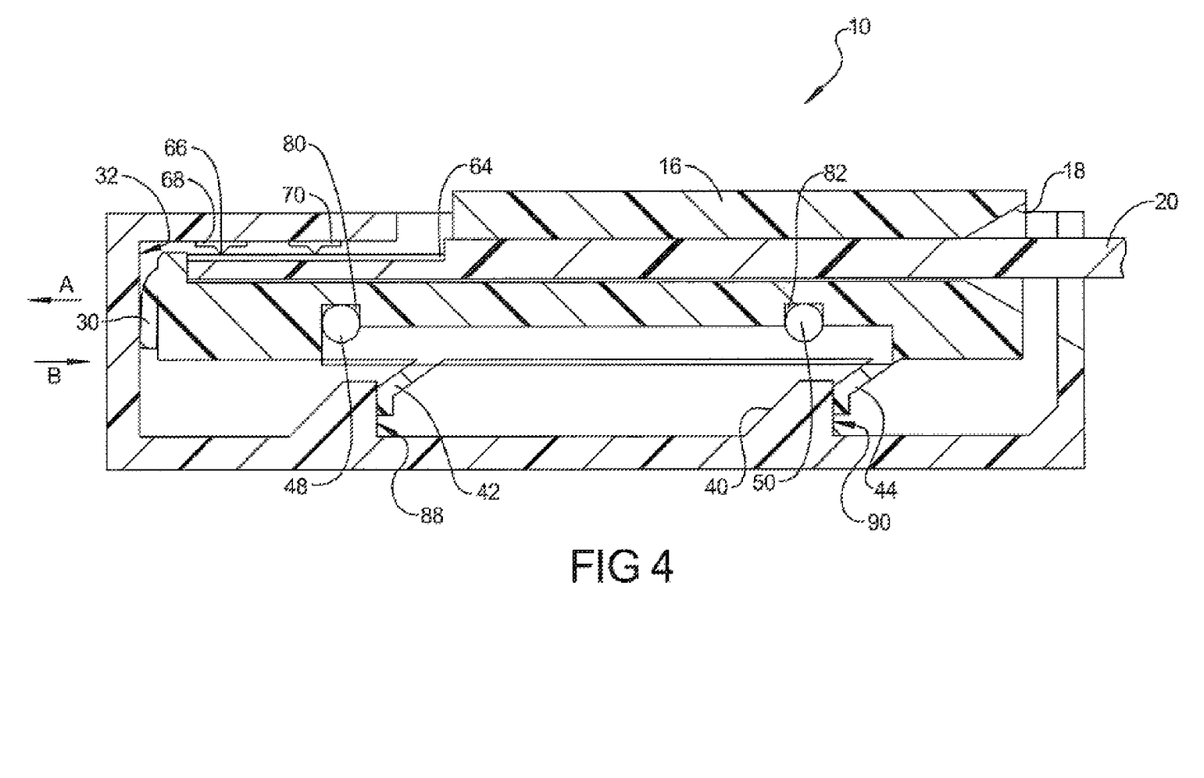
FIG. 4 shows a cross sectional side elevational view modified from FIG. 3 to show the carrier body following orthogonal displacement to an electrical contact engaged condition.

Carrier body 16 displacement in contact direction "C" resulting from the biasing force created in second and third biasing members 42, 44 is sufficient to rapidly displace the carrier body 16. The patient or user receives a tactile feedback as carrier body 16 displaces in the contact direction "C" and contacts the first and second contacts 68, 70. This tactile feedback to the user provides assurance that electrical contact has been created.

Referring to FIG. 5 and again to FIG. 4, after the user receives tactile indication of contact between strip conductors 64 and both of the first and second contacts 68, 70, the carrier body 16 will remain in the contact position until a test signal or test report is created. To subsequently eject strip 20, the user can manually press against a carrier body surface 92 of carrier body 16 in a contact release direction "E" which is oppositely directed with respect to contact direction "C". In further embodiments, the strip carrier 12 can be incorporated in a device housing (not shown) that can provide the user with a press-able button, a distendable area marked with a graphic or similar feature that the user can activate to eject strip 20. In the further embodiments no direct user contact with carrier body 16 is required. In the embodiments depicted, as carrier body 16 displaces in the contact release direction "E", each of the first and second guide rods 48, 50 are displaced from within the guide feature first and second branches 80, 82. Displacement in the contact release direction "E" occurs until the first and second guide rods 48, 50 directly contact the guide feature lower face 56 of guide feature 54. Displacement of carrier body 16 in the contact release direction "E" further recompresses/biases the second and third biasing members 42, 44 to preload these biasing members for a subsequent connector device operation. Because first biasing member 30 is maintained in sliding contact with housing second end face 32 during the sliding motion of carrier body 16 in the contact release direction "E", the biasing force of first biasing member 30 continues to act in the ejection direction "B". When carrier body support wall 36 again contacts both of the first and second raised stops 38, 40, contact clearance "D" is re-established.

Figure 5:
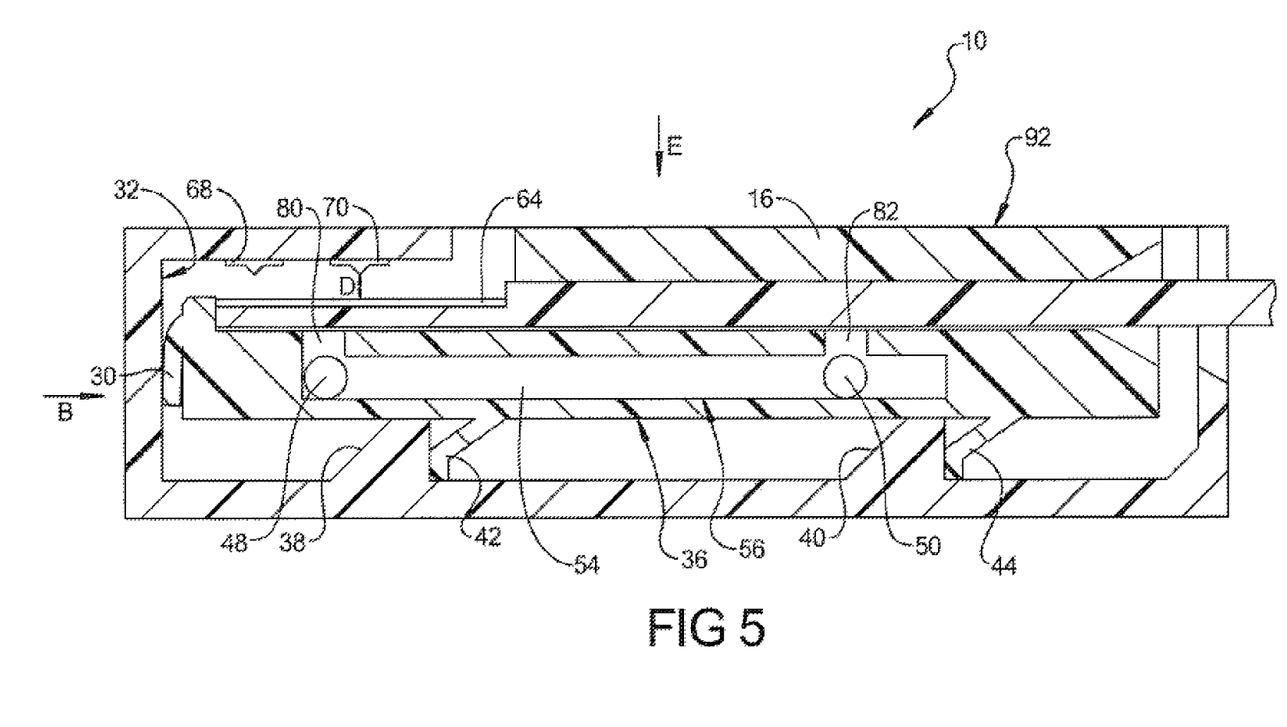
FIG. 5 shows a cross sectional side elevational view modified from FIG. 4 to show a carrier body release condition.
Figure 6:
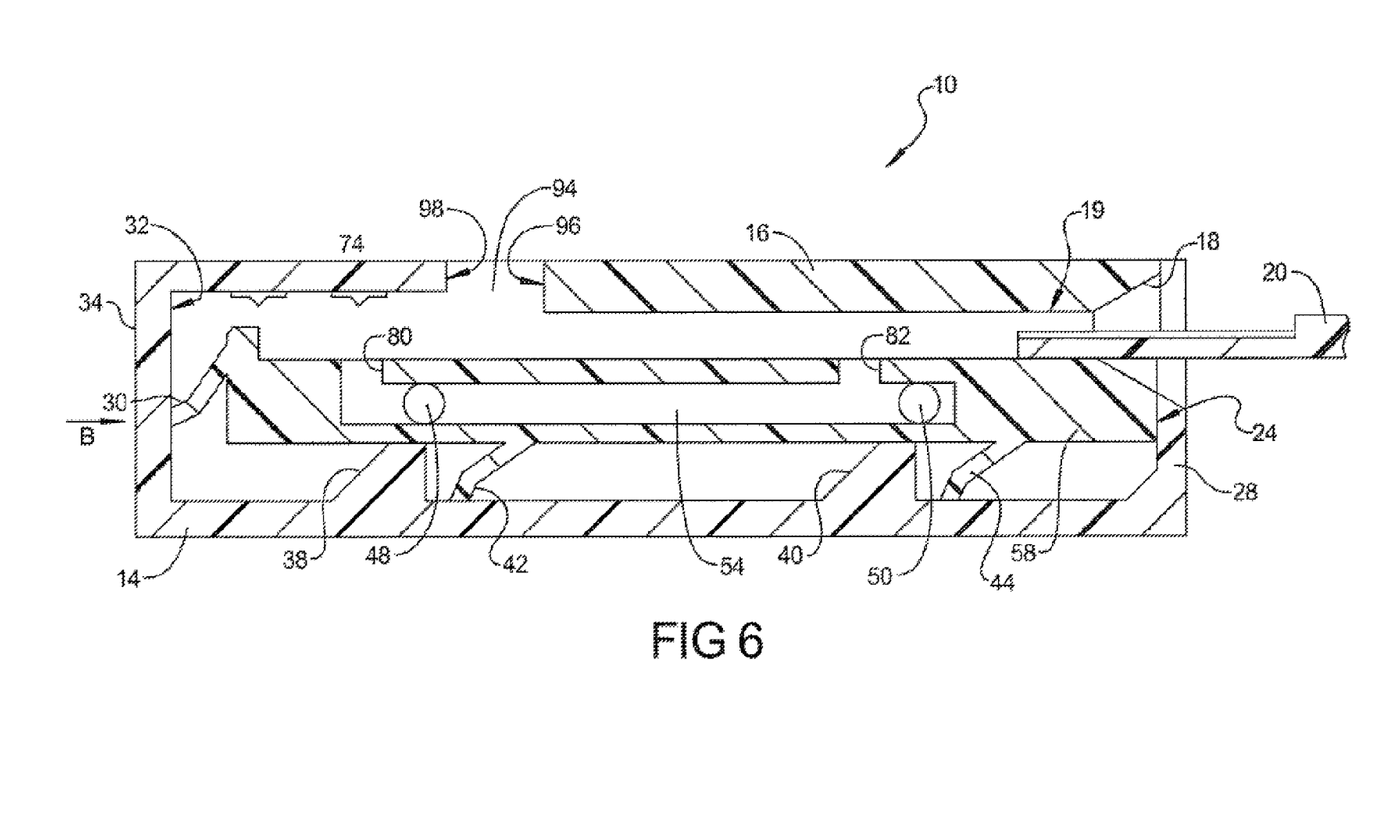
FIG. 6 shows a cross sectional side elevational view modified from FIG. 6 to show a test strip ejection condition.

Referring to FIG. 6 and again to FIG. 5, as soon as the first and second guide rods 48, 50 extend freely out of the guide feature first and second branches 80, 82, the biasing force of first biasing member 30 plus a portion of the biasing forces of second and third biasing members 42, 44 slides the carrier body 16 in the ejection direction "B" until carrier body first end face 24 of body lower portion 58 directly contacts housing first end wall 28. The amount of biasing force of first biasing member 30 is selected to rapidly displace carrier body 16. The rapid displacement of carrier body 16 also co-accelerates the strip 20 such that, as contact between carrier body first end face 24 and housing first end face 26 occurs, the velocity of strip 20 overcomes the frictional contact with the walls of longitudinal strip channel 19 and strip 20 freely ejects from longitudinal strip channel 19 and channel opening 18. Following ejection of strip 20, strip connector device 10 is substantially repositioned as shown in FIG. 2 and ready for a subsequent operation by insertion of a new strip. According to several embodiments, an opening 94 can be provided between a carrier body upper portion end face 96 and a housing upper wall end face 98 of housing upper wall 74. Opening 94 provides clearance between the housing upper wall 74 and carrier body 16 for motion of carrier body 16. The opening 94, when not visually blocked by structure of a contact strip housing (not shown) may also be available to visually determine that no portion of a previously used strip 20 is still retained within longitudinal strip channel 19 and/or that space is available to receive a new strip 20. When the opening 94 is not visible, protrusion of a dose end of the strip 20 provides visual indication of the position of strip 20.

Figure 7:
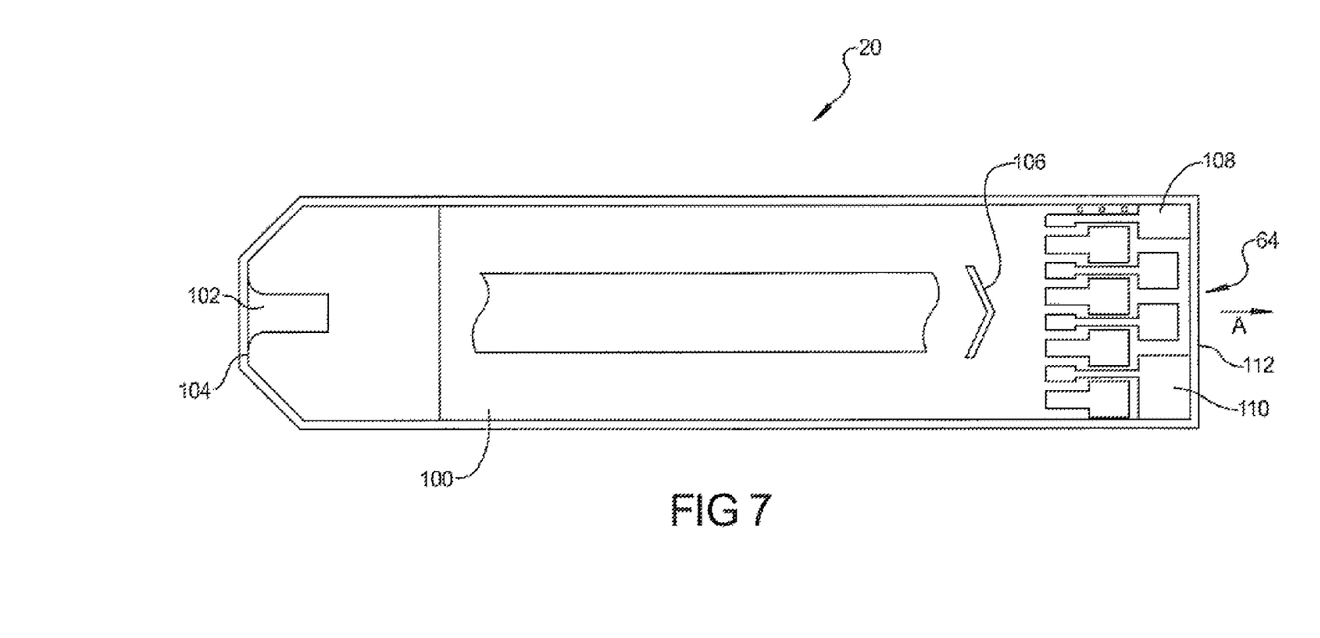
FIG. 7 shows a top plan view of an exemplary body fluid strip.

Referring to FIG. 7 and again to FIGS. 2 and 3, an exemplary body fluid test strip 20 includes a strip body 100 having a reagent portion 102 proximate to a strip first end 104. An insertion direction indicator 106 can be provided on strip body 100 to visually indicate to a user the direction of insertion "A" for insertion into strip connector device 10. First and second printed circuit portions 108, 110 of strip conductors 64 can be provided by etching, ablation, or the like process and located proximate to a strip second end 112. It should be evident that contact with the first and second printed circuit portions 108, 110 proximate strip second end followed by continued displacement of strip 20 in the insertion direction "A" can abrade or remove the material of first and/or second printed circuit portions 108, 110 which can result in faulty electrical contact. The present disclosure therefore provides direct contact with first and second printed circuit portions 108, 110 from a direction facing strip body 100 as viewed in FIG. 7 after strip 20 reaches the strip conductor alignment position shown in FIG. 3 to prevent contact with first and second printed circuit portions 108, 110 while strip 20 is still moving in the insertion direction "A"

Referring to FIG. 8 and again to FIG. 2, strip connector device 10, when separated into its component parts, further includes a strip carrier first side wall 114 which is oppositely positioned and oriented parallel with respect to a strip carrier second side wall 116. Each of the strip carrier first and second side walls 114, 116 include individual ones of the first and second guide rods 48, 50 integrally connected thereto and extending orthogonally outwardly therefrom. The first and second guide rods 48, 50 of strip carrier second side wall 116 are not clearly visible in this view, but form a mirror image configuration of the first and second guide rods 48, 50 of strip carrier first side wall 114. When strip carrier 12 is slidably received within connector housing 14, as previously noted, the first and second guide rods 48, 50 of each of the first and second side walls 114, 116 are each individually slidably disposed in one of the guide features 54, 54' created in first and second side walls 118, 120 of the connector housing 14. Strip carrier 12 further includes first and second strip stop members 122, 124 which define each of the strip contact walls 60. The first and second strip stop members 122, 124 are positioned in an open space between strip carrier first and second extending walls 126, 128 which each include a strip guide edge 129. The spacing between strip guide edges 129 of the strip carrier first and second extending walls 126, 128 slidably receive and axially align the strip 20 during its sliding motion within longitudinal strip channel 19.

Figure 8:
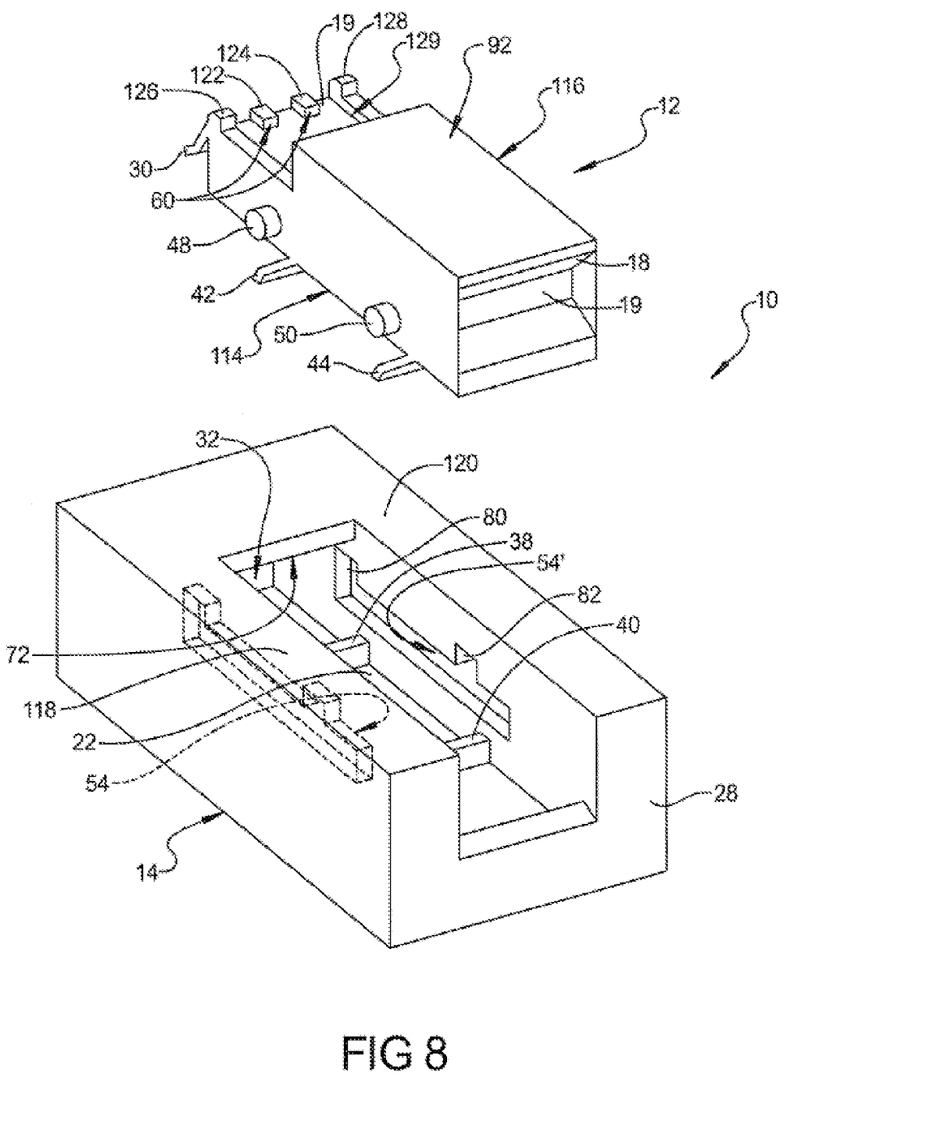
FIG. 8 shows a rear elevational assembly view of the strip connector device of FIG. 1.

According to several embodiments, the strip carrier 12 can be assembled with respect to connector housing 14 by outwardly elastically deflecting the connector housing first and second side walls 118, 120 to permit the first and second guide rods 48, 50 to be slidably received between connector housing first and second side walls 118, 120 which elastically rebound to their parallel positions shown when the first and second guide rods 48, 50 are received in the individual guide features 54, 54'. The first and second guide rods 48, 50 thereafter provide for retention of strip carrier 12 while also permitting sliding motion of strip carrier 12 with respect to connector housing 14. The male members or first and second guide rods 48, 50 can take multiple forms, such as tubular extensions, rounded extensions, or other geometric shapes. It is further noted that each of the second and third biasing members 42, 44 are configured to elastically deflect when the strip carrier 12 is received in connector housing 14. This elastic deflection provides the biasing force for subsequent displacement of the strip carrier 12 in the contact direction "C", previously described herein. Second and third biasing members 42, 44 as well as first biasing member 30 can be provided in multiple forms, including but not limited to planar, curved, or multi-planar bodies, coil springs, leaf springs, and the like. First, second and third biasing members 30, 42, 44 can be integrally connected, fixedly connected, releasably attached, or the like to strip carrier 12, and can also be individually provided as two or more biasing items which together perform the function of the individual biasing member.

Referring to FIG. 9 and again to FIGS. 2 and 8, according to additional embodiments, a strip connector device 130 is modified from strip connector device 10 to eliminate the requirement for first and second guide rods 48, 50 and therefore to eliminate the requirement for the guide features 54. Strip connector device 130 includes a connector housing 132 which slidably receives a strip carrier 134. Connector housing 132 includes a housing upper wall 136 which provides at least one and according to several embodiments a plurality of electrical contacts 138. The strip carrier 134 is initially slidably received within a housing open end 140 and restrained against removal in the contact direction "C" by oppositely positioned housing side walls 142 (only a first one of housing side walls 142 is visible in this view). Each of the housing side walls 142 are mirror images of the other and include first and second branches or side wall slots 144, 146 which are upwardly recessed with respect to a side wall lower face 148 as viewed in FIG. 9. A third side wall slot 150, which can be recessed to a lesser height with respect to side wall lower face 148, opens into second side wall slot 146. The third side wall slot 150 includes a slot end wall 152.

Figure 9:
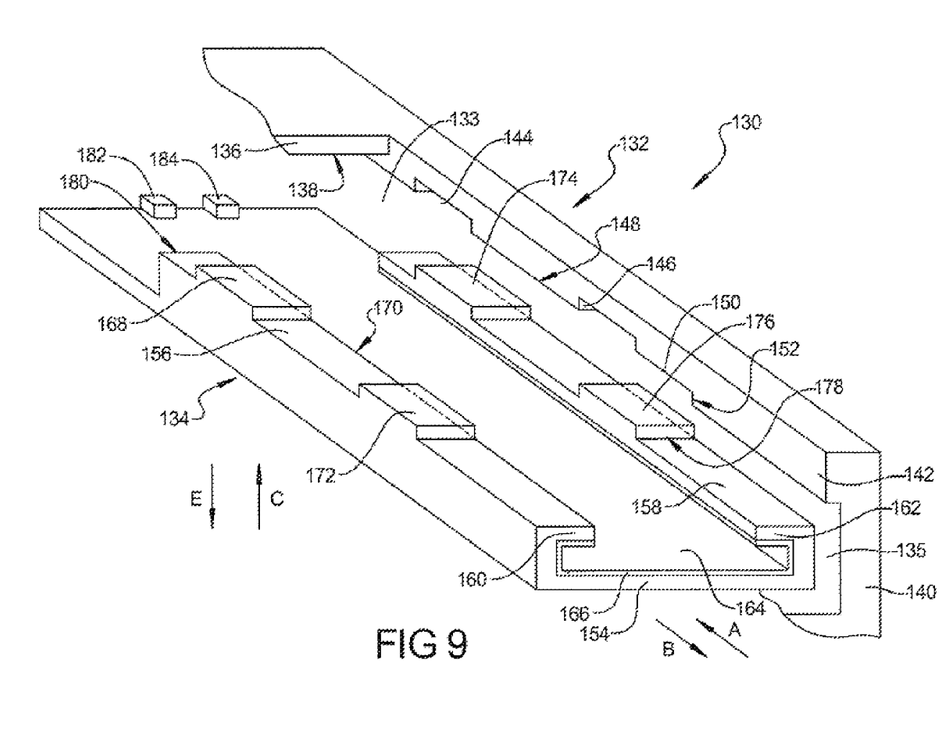
FIG. 9 shows a rear elevational assembly view of a further embodiment of a strip connector device of the present disclosure.

The strip carrier 134 of strip connector device 130 includes a substantially planar carrier body 154 having opposed, generally U-shaped first and second carrier side walls 156, 158. Each of the first and second carrier side walls 156, 158 includes one of a first or second overhang wall portion 160, 162. A strip channel 164 is formed between first and second carrier side walls 156, 158, and a strip 20 is slidably retained within the strip channel 164 by the first and second overhang wall portions 160, 162 for a portion of a sliding distance of the strip within strip channel 164. The strip carrier 134 also includes a beveled channel edge 166 at an inlet to the strip channel 164 to help align the strip between the first and second carrier side walls 156, 158 for sliding displacement in the insertion direction "A". Each of the first and second carrier side walls 156, 158 include raised bosses which when aligned with individual ones of the first and second side wall slots 144, 146 are received in a similar manner that first and second guide rods 48, 50 were received within the guide feature first and second branches 80, 82 as described in reference to FIG. 4. These bosses include a first side wall first raised boss 168 which extends from a first side wall upper surface 170 and a first side wall second raised boss 172 which also extends from first side wall upper surface 170. Similarly, second carrier sidewall 158 includes each of a second side wall first raised boss 174 and a second sidewall second raised boss 176. Each of the first and second side wall first and second raised bosses 168, 172, 174, 176 are positioned in sliding contact with the side wall lower face 148 until the individual bosses align with individual ones of the first or second side wall slots 144, 146. At this time the biasing force of the second and third biasing members 42', 44' displace the bosses into the respective ones of the first or second side wall slots 144, 146, which permits direct contact between the strip and the contacts 138.

Once contact with the electrical contacts 138 is completed the strip carrier 134 is manually displaced in the contact release direction "E". At this time the biasing force of first biasing member 30', together with a biasing force of second and third biasing members 42', 44' acting in the ejection direction "B" displace the strip carrier 134 in the ejection direction "B" until the boss stop face 178 of the first side wall second raised boss 172 and the second side wall second raised boss 176 contact the slot end wall 152 of third side wall slot 150 of each of the housing side walls. Contact between boss stop face 178 and slot end wall 152 prevents the total removal of the strip carrier 134 with respect to connector housing 132 in the ejection direction "B", but permits the continued ejection of the individual strip 20.

Each of the first and second carrier side walls 156, 158 include an overhang end face 180 which provides an open or free space proximate to each of a first and second strip stop members 182, 184 extending upwardly from a free end of planar carrier body 154. The first and second strip stop members 182, 184, similar to the first and second strip stop members 122, 124, act as a sliding stop for the strip 20 as the strip completes its sliding displacement through strip channel 164, and position the printed circuit board portions of strip 20 in alignment with the electrical contacts 138.

During use, a strip connector device 10, 130 of the present disclosure receives a body fluid test strip 20 to measure a biologic fluid applied to the test strip 20. The strip connector device 10, 130 includes the connector housing 14, 132 having a cavity 22, 133 and a male member guide feature 54, 135. A strip carrier 12, 134 is slidably disposed in the cavity 22, 133 of the connector housing 14, 132. The strip carrier 12, 134 includes a carrier body 16 having a longitudinal strip channel 19, 164 configured to slidably receive the test strip 20 in the insertion direction "A". The first biasing member 30, 30' is positioned between the strip carrier 12, 134 and the connector housing 14, 132 and acts to bias the strip carrier 12, 134 in the ejection direction "B" oppositely directed with respect to the insertion direction "A". At least one second biasing member 42, 42' contacts the carrier body 16 and is in sliding contact with the connector housing 14, 132. The at least one second biasing member 42, 42' acts orthogonally with respect to the first biasing member 30, 30' and acts to bias the carrier body 16 in the contact direction "C" which is orthogonally oriented with respect to the ejection direction "B". The male member (first and/or second guide rods 48, 50 or the first sidewall first and second raised bosses 168, 172, and/or the second sidewall first and second raised bosses 174, 176) outwardly extend from the carrier body 16 and is/are slidably received with respect to the guide feature 54, 135 created in the connector housing 14, 132. The male member is in contact with a wall (guide feature upper face 52 or side wall lower face 148) of the guide feature 54, 135 thereby preventing displacement of the strip carrier 12, 134 in the contact direction "C" until the male member is axially aligned with and received in the guide feature branch (guide feature first/second branches 80, 82 or first/second side wall slots 144, 146) extending orthogonally with respect to the guide feature 54, 135.

First and second electrical contacts (68, 70, 138) are connected to the connector housing 14, 132. The first and second electrical contacts (68, 70, 138) are each individually contacted by a strip conductor 64 of the test strip 20 when the strip carrier 12, 134 is displaced in the contact direction "C" by the second biasing member (42, 42') and/or the third biasing member (44, 44'), thereby defining a strip conductor contact position (shown in FIG. 4). Electrical contact is made with the test strip by moving the test strip in the contact direction "C" which is orthogonally oriented with respect to the insertion direction "A" and/or the ejection direction "B". After electrical contact is made with the test strip 20, the strip carrier 12, 134 is manually displaced in the contact release direction "E", elastically biasing the second and third biasing members (42, 42', 44, 44') until the male members are displaced out of the guide feature 54, 135. The first biasing member 30, 30' thereafter displaces the strip carrier 12, 134 and the test strip 20 in the ejection direction "B". A velocity of both the strip carrier (12, 134) and the test strip 20 achieved when both are displaced in the ejection direction "B" is maintained by the test strip 20 after the strip carrier (12, 134) contacts housing first end wall 28 or when the boss stop faces 178 contact the slot end walls 152. This retained velocity permits test strip 20 to be thereby ejected from the strip carrier (12, 134). Optionally, test strip 20 can also be manually removed from the strip carrier (12, 134).

The broad teachings of the disclosure can be implemented in a variety of forms. Therefore, while this disclosure includes particular examples, the true scope of the disclosure should not be so limited since other modifications will become apparent to the skilled practitioner upon a study of the drawings, the specification, and the following claims.

This detailed description is merely illustrative in nature and is in no way intended to limit the disclosure, its application, or uses. For purposes of clarity, the same reference numbers are used in the drawings to identify similar elements. As used herein, the phrase at least one of A, B, and C should be construed to mean a logical (A or B or C), using a non-exclusive logical or. It should be understood that steps within a method can be executed in different order without altering the principles of the present disclosure.

The apparatuses and methods described herein can be implemented by one or more computer programs or applications executed by one or more processors. The computer programs and applications can include processor-executable instructions that are stored on a non-transitory tangible computer readable medium. The computer programs can also include stored data. Non-limiting examples of the non-transitory tangible computer readable medium are non-volatile memory, magnetic storage, and optical storage.

What is claimed is:

1. A strip connector receiving a body fluid test strip to measure a biologic fluid applied to the test strip, the strip connector comprising:
    a connector housing having a housing cavity;
    a strip carrier movably disposed in the housing cavity of the connector housing, the strip carrier including a carrier body having a longitudinal channel configured to slidably receive a body fluid test strip in an insertion direction;
    a first biasing member positioned between the strip carrier and the connector housing and acting to bias the strip carrier in an ejection direction oppositely directed with respect to the insertion direction;
    a second biasing member positioned between the strip carrier and the connector housing and orthogonally acting with respect to the first biasing member, the second biasing member acting to bias the carrier body in a contact direction orthogonally oriented with respect to the ejection direction;

wherein the connector housing further includes a longitudinally extending guide feature having a first branch oriented orthogonally with respect to the guide feature; and wherein the strip carrier further includes a first guide rod outwardly extending from the carrier body and slidably received in the guide feature created in the connector housing, the first guide rod permitting sliding motion of the strip carrier parallel with the guide feature but preventing displacement of the strip carrier in a contact direction orthogonal to the guide feature until the first guide rod is axially aligned with the first branch of the guide feature extending orthogonally with respect to the guide feature.

2. The strip connector of claim 1, further including electrical contacts connected to the connector housing, wherein each of the electrical contacts is individually contacted by a strip conductor of the test strip when the first guide rod is displaced into the first branch of the guide feature when the strip carrier is displaced in the contact direction by the second biasing member.

3. The strip connector of claim 1, wherein the longitudinally extending guide feature includes a second branch oriented orthogonally with respect to the guide feature.

4. The strip connector of claim 1, wherein the strip carrier further includes a second guide rod outwardly extending from the carrier body and slidably received in the guide feature, the first and second guide rods together permitting sliding motion of the strip carrier parallel with the guide feature but preventing displacement of the strip carrier in the contact direction orthogonal to the guide feature until the first guide rod is axially aligned with and received in the first branch of the guide feature and the second guide rod is axially aligned with and received in a second branch of the guide feature when the strip carrier is displaced in the contact direction by the second biasing member.

5. The strip connector of claim 1, wherein the guide feature is a recessed channel.

6. The strip connector of claim 1, further including a third biasing member positioned between the strip carrier and the connector housing and orthogonally acting with respect to the first biasing member, the third biasing member acting together with the second biasing member to bias the carrier body in the contact direction orthogonally oriented with respect to the ejection direction.

7. The strip connector of claim 1, wherein the connector housing further includes:

electrical contacts connected to the connector housing, wherein each of the electrical contacts is individually contacted by a strip conductor of the test strip when the strip carrier is displaced in the contact direction by the second biasing member; and a raised stop extending into the housing cavity from the connector housing, the raised stop when contacted by the second biasing member defining a strip conductor alignment position of the strip carrier having the strip conductor aligned with the electrical contacts, the second biasing member deflecting upon contact with the raised stop to create a biasing force acting together with the first biasing member to bias the strip carrier in the ejection direction.

8. The strip connector of claim 1, wherein the second biasing member is further partially deflectable by motion of the strip carrier in the insertion direction thereby biasing the carrier body in the ejection direction.

9. The strip connector of claim 1, wherein the first and second biasing members are integrally connected to the strip carrier and in sliding contact with the connector housing.

10. A strip connector receiving a body fluid test strip to measure a biologic fluid applied to the test strip, the strip connector comprising:

a connector housing having a housing cavity and a guide feature;

a strip carrier slidably disposed in the housing cavity of the connector housing, the strip carrier including a carrier body having a longitudinal channel configured to slidably receive a test strip in an insertion direction;

a first biasing member positioned between the strip carrier and the connector housing and acting to bias the strip carrier in an ejection direction oppositely directed with respect to the insertion direction;

at least one second biasing member contacting the carrier body and in sliding contact with the connector housing, the at least one second biasing member orthogonally acting with respect to the first biasing member and acting to bias the carrier body in a contact direction orthogonally oriented with respect to the ejection direction; and a male member outwardly extending from the carrier body and slidably received with respect to the guide feature created in the connector housing, the male member in contact with a wall of the guide feature preventing displacement of the strip carrier in the contact direction until the male member is axially aligned with and received in a guide feature branch extending orthogonally with respect to the guide feature.

11. The strip connector of claim 10, further including a carrier body first end face adapted to contact a connector housing first end face.

12. The strip connector of claim 11, further including a carrier body second end face oppositely directed with respect to the carrier body first end face, the first biasing member extending from the carrier body second end face and in contact with a connector housing second end face.

13. The strip connector of claim 12, wherein the second biasing member extends from a carrier body support wall orthogonally oriented with respect to the first and second housing end faces.

14. The strip connector of claim 10, further including first and second electrical contacts connected to the connector housing and individually contacted by a strip conductor of the test strip when the male member is received in the guide feature branch and the strip carrier is displaced in the contact direction by the at least one second biasing member.

15. The strip connector of claim 10, wherein the connector housing further includes a raised stop extending into the housing cavity from the connector housing, the raised stop contacted by the at least one second biasing member defining a strip conductor alignment position of the strip carrier, the at least one second biasing member deflecting upon contact with the raised stop to create a biasing force acting together with the first biasing member to bias the strip carrier in the ejection direction.

16. A strip connector receiving a body fluid test strip to measure a biologic fluid applied to the test strip, the strip connector comprising:

a connector housing having a housing cavity;

a strip carrier slidably disposed in the housing cavity of the connector housing, the strip carrier including a carrier body having:
- a longitudinal strip channel configured to slidably receive a test strip in an insertion direction;
- a first biasing member positioned between the strip carrier and the connector housing and acting to bias the strip carrier in an ejection direction oppositely directed with respect to the insertion direction; and
- a second biasing member positioned between the strip carrier and the connector housing, the second biasing member in a first mode orthogonally acting with respect to the first biasing member to bias the carrier body in a contact direction orthogonally oriented with respect to the ejection direction; and the second biasing member being further partially deflectable by motion of the strip carrier in the insertion direction, the second biasing member in a second mode acting to bias the carrier body in the ejection direction together with the first biasing member.

17. The strip connector of claim 16, wherein the connector housing further includes a longitudinal guide channel oriented parallel with the insertion direction.

18. The strip connector of claim 17, wherein the carrier body includes first and second male members outwardly extending from the carrier body and slidably received with respect to the guide channel of the connector housing.

19. The strip connector of claim 18, wherein the connector housing further includes guide channel first and second branches opening into and extending orthogonally with respect to the guide channel, the first and second male members when positioned in sliding contact with the guide channel preventing displacement of the carrier body in the contact direction orthogonal to the guide channel until the first and second male members are axially aligned with the guide channel first and second branches, the second biasing member thereafter acting to displace the first and second male members into the guide channel first and second branches and the strip carrier in the contact direction.

20. The strip connector of claim 18, further including electrical contacts connected to the connector housing, wherein each of the electrical contacts is individually contacted by a strip conductor of the test strip when the first and second male members are axially aligned with and displaced into the guide channel first and second branches and the strip carrier is displaced in the contact direction by the second biasing member.

21. The strip connector of claim 16, wherein the connector housing further includes a raised stop extending into the housing cavity from the connector housing, the carrier body in sliding contact with the raised stop in each of the insertion and ejection directions and displaced from the raised stop during displacement in the contact direction.

22. A strip connector receiving a body fluid test strip to measure a biologic fluid applied to the test strip, the strip connector comprising:
- a connector housing having a housing cavity;
- a strip carrier movably disposed in the housing cavity, the strip carrier including a carrier body having a longitudinal strip channel configured to slidably receive a test strip in an insertion direction;
- a first biasing member positioned between the strip carrier and the connector housing and acting to bias the strip carrier in an ejection direction oppositely directed with respect to the insertion direction; and
- a second biasing member contacting the carrier body and in sliding contact with the connector housing, the second biasing member acting orthogonally with respect to the first biasing member to bias the carrier body in a contact direction orthogonally oriented with respect to the ejection direction; and
- first and second electrical contacts connected to the connector housing, wherein each of the first and second electrical contacts is individually contacted by a strip conductor of the test strip when the strip carrier is displaced in the contact direction by the second biasing member to a strip conductor contact position.

23. The strip connector of claim 22, wherein the connector housing further includes a raised stop extending into the housing cavity from the connector housing, the raised stop contacted by the second biasing member defining a strip conductor alignment position of the strip carrier having the strip conductor aligned with the first and second electrical contacts.

24. The strip connector of claim 23, wherein the second biasing member is deflected upon contact with the raised stop to create a biasing force acting together with the first biasing member to bias the strip carrier in the ejection direction.

25. The strip connector of claim 23, wherein:
- the connector housing further includes a longitudinal guide feature oriented parallel to the insertion direction; and
- the carrier body includes a guide rod outwardly extending from the carrier body and slidably received in the guide feature created in the connector housing, the guide rod preventing displacement of the carrier body in the contact direction until the carrier body reaches the strip conductor alignment position.

26. The strip connector of claim 25, wherein the connector housing further includes a guide feature branch opening into and extending orthogonally with respect to the guide feature, the guide rod when positioned in the guide feature preventing displacement of the carrier body in the contact direction orthogonal to the guide feature until the guide rod is axially aligned with the guide feature branch, the second biasing member thereafter acting to displace the guide rod into the guide feature branch and the strip carrier in the contact direction.

* * * * *